(12) United States Patent
Hommann

(10) Patent No.: US 7,749,195 B2
(45) Date of Patent: Jul. 6, 2010

(54) ADMINISTRATION DEVICE WITH AN INSERTION MECHANISM AND A DELIVERY MECHANISM

(75) Inventor: Edgar Hommann, Grossaffoltern (CH)

(73) Assignee: TecPharma Licensing AG, Burgdorf (CH)

( * ) Notice: Subject to any disclaimer, the term of this patent is extended or adjusted under 35 U.S.C. 154(b) by 636 days.

(21) Appl. No.: 11/372,974

(22) Filed: Mar. 10, 2006

(65) Prior Publication Data

US 2008/0009807 A1    Jan. 10, 2008

Related U.S. Application Data

(63) Continuation of application No. PCT/CH2004/000565, filed on Sep. 8, 2004.

(30) Foreign Application Priority Data

Sep. 11, 2003  (DE)  ................ 103 42 059

(51) Int. Cl.
*A61M 5/20* (2006.01)
*A61M 5/315* (2006.01)
(52) U.S. Cl. .................. 604/135; 604/218
(58) Field of Classification Search ........... 604/187, 604/131–137, 158, 68–72, 218
See application file for complete search history.

(56) References Cited

U.S. PATENT DOCUMENTS

| 5,176,643 | A |   | 1/1993 | Kramer et al. |
|---|---|---|---|---|
| 5,320,609 | A | * | 6/1994 | Haber et al. ............. 604/135 |
| 6,280,421 | B1 |   | 8/2001 | Kirchhofer et al. |
| 6,575,939 | B1 | * | 6/2003 | Brunel .................. 604/187 |
| 7,361,160 | B2 | * | 4/2008 | Hommann et al. ......... 604/198 |

FOREIGN PATENT DOCUMENTS

| WO |     0247746 A1 | 6/2002 |
|---|---|---|
| WO | 2004047893 A1 | 6/2004 |

* cited by examiner

*Primary Examiner*—Matthew F Desanto
(74) *Attorney, Agent, or Firm*—Dorsey & Whitney LLP; David E. Bruhn

(57) ABSTRACT

A device for administering an injectable product including an insertion mechanism for inserting an injection needle into a tissue, the insertion mechanism including a first pressure element, a delivery mechanism for delivering the product from a product container, the delivery mechanism including a second pressure element, and a trigger for triggering the insertion and delivery mechanisms, wherein, when triggered, the insertion mechanism is moved by the first pressure element in an insertion direction from an initial position to an insertion position and the delivery mechanism remains at rest relative to the insertion mechanism until the insertion position is reached.

12 Claims, 3 Drawing Sheets

ADMINISTRATION DEVICE WITH AN INSERTION MECHANISM AND A DELIVERY MECHANISM

CROSS-REFERENCE TO RELATED APPLICATION

This application is a continuation of International Application No. PCT/CH2004/000565, filed on Sep. 8, 2004, which claims priority to German Application No. 103 42 059.2, filed on Sep. 11, 2003, the contents of which are incorporated in their entirety be reference herein.

BACKGROUND

The present invention relates to devices and methods for delivering, administering or injecting a substance, and to methods of making and using such devices. More particularly, it relates to a device for administering an injectable product, more particularly to an auto-injection device, comprising an insertion mechanism for inserting an injection needle and a delivery mechanism for delivering the injectable product.

Administering devices for automatically administering an injectable product, such as insulin, growth hormones or the like, with one hand are known in many various embodiments. They generally comprise an actuator, e.g., a button, trigger or the like which is pushed, pressed or pulled, an insertion means for inserting an injection needle into a body tissue and a delivery means which delivers the injectable product from a product container of the administering device after the injection needle has been inserted. The insertion and delivery means can be activated by manipulating a trigger, e.g. by hand, such that first an insertion movement of the injection needle and then a delivery movement for delivering the product is performed.

To this end, both the insertion means and the delivery means are provided with a force-generating drive mechanism, e.g., a spiral spring, which is clamped between the insertion and/or delivery means and an abutment, e.g., on or part of the casing of the administering device. The insertion and delivery means can be fixed when the drive mechanisms are tensed, and released or actuated by the trigger. Triggering the insertion and/or delivery means drives them in an insertion direction, i.e., generally along or parallel to the longitudinal axis of the device towards the body tissue.

An exemplary device, an injection pistol, is disclosed in DE 35 27 290 A1. An injection needle is fastened in a casing to a cylinder which can be moved relative to the casing and which can be driven by a spiral spring and moved to a biased position. A piston is arranged within the cylinder and can be moved with respect to the casing, driven by a second spiral spring, and likewise moved to a biased position. The piston and the cylinder interact in such a way that when the injection pistol is triggered, the cylinder is triggered first in order to cause the injection needle to be inserted, and then the piston is triggered in order to cause a product dosage to be delivery into a tissue. The first and second spiral spring are arranged co-axially along the longitudinal axis of the injection pistol. When triggered, the spring driving the cylinder together with the needle is triggered first, and the second spring, acting on the piston, and the piston initially remain at rest with respect to the casing. Once the cylinder has overcome a predetermined distance, the second spring is triggered by the cylinder, such that a delivery is performed. In the injection pistol, both springs are arranged in a fixed position relative to each other and with respect to the casing. Despite a separate drive, on the one hand for the cylinder for inserting and on the other for the piston for delivering, a relative movement takes place during insertion between the cylinder movement for inserting and the piston movement for delivering, such that insertion and delivery cannot be performed completely independently of each other.

SUMMARY

It is an object of the present invention to provide a device or apparatus for administering an injectable product, in which the delivery of the product is not affected or disrupted by an insertion process for inserting an injection needle carried by the device into a tissue, and which ensures that the insertion process and delivery are reliably separated when automatically administering.

In one embodiment, the present invention comprises a device for administering or injecting an injectable product comprising an insertion mechanism for inserting an injection needle into a tissue, the insertion mechanism comprising a first pressure element, a delivery mechanism for delivering the product from a product container, the delivery mechanism comprising a second pressure element, and a trigger for triggering the insertion and delivery mechanisms, wherein, when triggered, the insertion mechanism is moved by the first pressure element in an insertion direction from an initial position to an insertion position and the delivery mechanism remains at rest relative to the insertion mechanism until the insertion position is reached.

In one embodiment, the present invention comprises a device for administering an injectable product, comprising insertion means for inserting an injection needle into a tissue, said insertion means comprising a first pressure element, delivery means for delivering said product from a product container, said delivery means comprising a second pressure element, and a trigger for triggering said insertion and delivery means, wherein when said insertion and delivery means are triggered, said insertion means is moved by said first pressure element in an insertion direction from an initial position to an insertion position and said delivery means is at rest relative to the insertion means until said insertion position is reached.

In a device for administering an injectable product, an insertion means for inserting an injection needle into a tissue is driven by a first pressure element and a delivery means for delivering the injectable product from a product container is driven by a second pressure element. In some embodiments, the pressure elements may preferably be spiral springs, but they can also be formed by other pressure-generating elements, for example gas springs. The springs may preferably generate a pressure by being compressed. It would, however, also be conceivable to cause a pressure to be generated by expanding the springs. The structural design of the administering device along the longitudinal axis of the device, e.g., with respect to the points of application of the springs and a trigger for the springs, must then be adapted to this way of generating a pressure. For triggering the insertion and delivery means, a trigger is arranged on the administering device. In some preferred embodiments, a single trigger is provided which, when activated, triggers both the insertion means and the delivery means. This enables the product to be automatically administered using one hand. In principle, however, it is also conceivable to provide each of the means with a trigger of its own.

When the insertion and delivery means is triggered, the insertion means is moved by the first pressure element in the insertion direction (toward the needle tip) from an initial position up to an insertion position. The insertion means thus moves relative to a casing of the administering device, along the longitudinal axis of the device towards the surface of the tissue, until the injection needle has penetrated into the surface of the tissue and the insertion means is therefore in an insertion position. The insertion position of the insertion means can be determined by an insertion stopper associated with the insertion means, for instance on a casing part. While the insertion means is moving, the delivery means remains at rest relative to the insertion means until the insertion position of the insertion means is reached. The delivery means then moves relative to the casing of the administering device simultaneously with the insertion means. While the insertion means is driven, i.e., while the first pressure element is acting on the insertion means, the second pressure element for driving the delivery means remains at rest, i.e., in its biased or tensioned position. Once the insertion position of the insertion means has been reached, the delivery means is moved in the insertion direction relative to the insertion means by means of the second pressure element into a delivery position. The delivery means is therefore moved along the longitudinal axis of the administering device towards the tissue, for delivering the injectable product, and is thus shifted relative to the insertion means and the casing of the administering device.

In an administering device in accordance with the present invention, the delivery means as a whole is moved during the insertion movement of the insertion means, such that no changes are caused within the delivery means by inserting the injection needle. The delivery means as a whole remains at rest during the insertion process. Only once the insertion process is concluded is the delivery means triggered and the injectable product delivered. The insertion and delivery processes are substantially separate. The two processes cannot therefore negatively affect each other. Setting the magnitude of a product dosage, for example, remains unaffected by the insertion process. Using the administering device as set forth in the present invention, therefore, the injectable product can be reliably and simply administered.

In a preferred embodiment of an administering device in accordance with the present invention, the insertion means comprises an injection needle and at least one drive sleeve in which at least the delivery means but also the product container and the second pressure element are accommodated. The drive sleeve can be formed from a number of sleeves which are attached and co-operate. In an initial position of the insertion means, the injection needle and the drive sleeve are arranged within a casing of the administering device. The injection needle is arranged at a front end of the drive sleeve lying opposite the surface of a tissue when a product is administered, and at the opposite rear end, away from the surface of the tissue, the first pressure element—in the form of a spiral spring—is supported against a casing part and acts on the drive sleeve.

The delivery means comprises a drive member, e.g., in the form of a piston rod, which acts on a piston in the product container. The drive member of the delivery means can be moved in the longitudinal direction of the administering device, relative to the drive sleeve of the insertion means. The second pressure element, in the form of a spiral spring, acts on the drive member and on the rear end of the drive sleeve. The product container is mounted at the front end within the drive sleeve. The second pressure element is therefore mounted within the drive sleeve together with the delivery means and can be moved with it.

The delivery means is fixed to the insertion means by a latching device. To this end, locking segments are provided, for example between the drive member of the delivery means and the drive sleeve of the insertion means, which, in an insertion position of the insertion means, co-operate with a releasing device in order to release the delivery means. The releasing device for releasing the locking segments is arranged on the insertion stopper of the insertion means. The latching device is therefore not released until the insertion process of the insertion means has been concluded.

In an initial position of the administering device, the drive member of the delivery means is held by a trigger which is supported with respect to the casing of the administering device. The first and second pressure element are held in a biased position. After triggering, i.e., after the drive member is released from the trigger, the first pressure element of the insertion means exerts a force on the drive sleeve. This shifts the drive sleeve in the insertion direction, relative to the casing of the administering device, until it abuts the insertion stopper. This shifts the injection needle out of the front end of the casing and, if the administering device is placed on a tissue, inserts the needle into the tissue. The administering device is then in an insertion position. The second pressure element remains at rest, since the drive member is fixed with respect to the drive sleeve. In the insertion position, the latching device between the drive sleeve and the drive member on the insertion stopper is released and the drive member moves in the insertion direction relative to the drive sleeve and drives the piston within the product container, such that the injectable product is administered from the container, through the injection needle. It is then possible to deliver all the product from the product container or to dispense only a predetermined product dosage. After the product has been delivered, the administering device is in a delivery position.

The strength of the first and second pressure element can be adapted to the respective use, e.g., the first spring for the insertion means can be selected to be significantly stronger than the second spring for delivering the product.

In some embodiments, an administering device in accordance with the present invention is preferably reusable, i.e., it can be returned to an initial state with a tensed first and second pressure element and, after a product container has been emptied, a new filled product container can be inserted.

DETAILED DESCRIPTION

Figure 1:
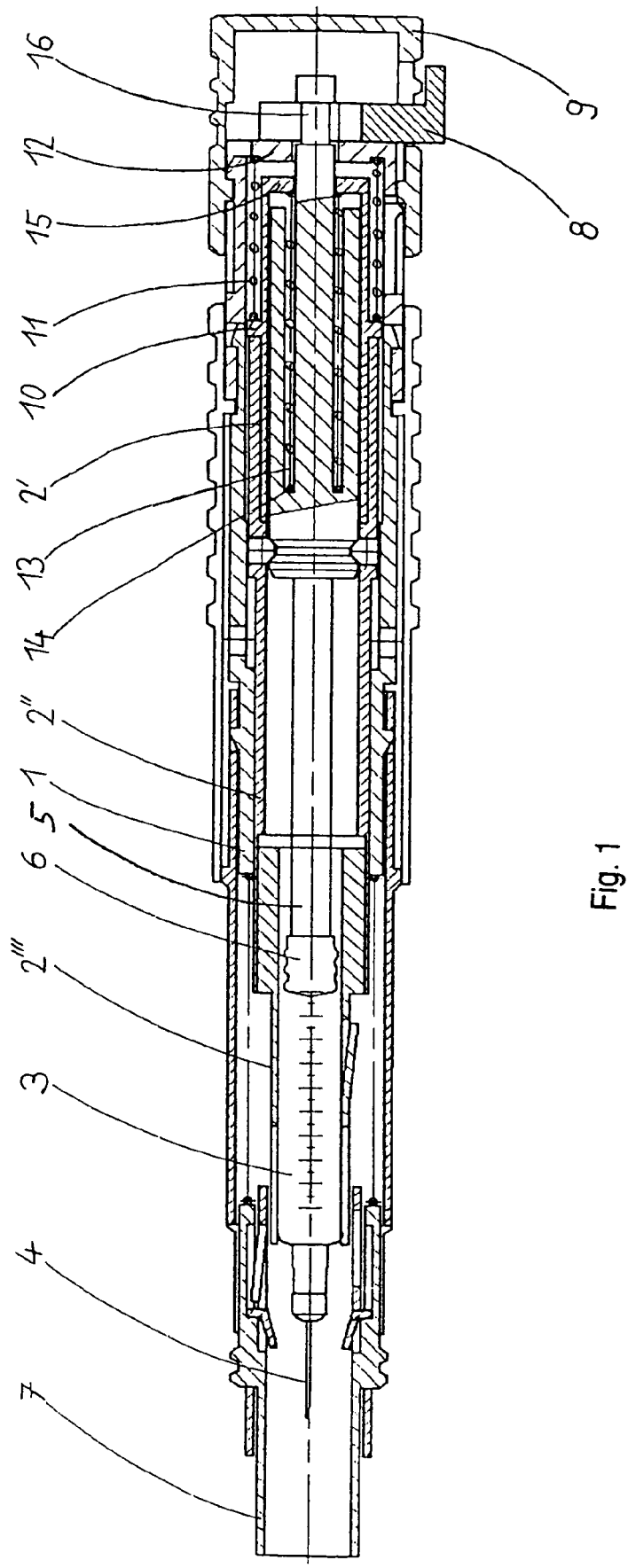
FIG. 1 is a longitudinal section through an administering device in accordance with the present invention in an initial position.

FIG. 1 shows an embodiment of an administering device in accordance with the present invention, comprising a casing 1 in which a drive sleeve 2 is accommodated. The drive sleeve 2 may comprise generally co-axially arranged sleeve parts or components 2', 2" and 2'". In the sleeve part 2'", a product container 3 in the form of an ampoule is inserted, which is connected to an injection needle 4 in such a way that the injection needle 4 protrudes out of the sleeve part. A drive member 5 in the form of a piston rod is arranged within the sleeve parts 2' and 2" and is connected to or abuts a piston 6 in the ampoule 3. A needle protecting sleeve 7, arranged at the front end of the casing 1 surrounding the injection needle 4, serves to protect or cover the needle after the product has been administered and is mounted such that it can be shifted along the casing. A trigger 8 for triggering the drive sleeve 2 and the piston rod 5, provided at the opposite, rear end of the casing 1, protrudes laterally out of the casing of the administering device and can be secured by a safety cap 9. The functionality of the trigger 8 and the safety cap 9 is described in detail in a parallel application owned by the owner of the present application and entitled "Administering device for an injectable product comprising a trigger safety device", which is incorporated herein by reference.

The sleeve part 2' of the drive sleeve 2 comprises a protrusion 10. A first spring 11, as the first pressure element, is mounted between the protrusion 10 and a wall 12 fixed to the casing. The drive sleeve 2 and the first spring 11, together with the injection needle 4, form the insertion means.

In its rear region within the sleeve part 2', the piston rod 5 comprises a recess 13 which runs or extends annularly with respect to the axis of the administering device, is open from the rear facing side of the piston rod, and extends in the longitudinal direction of the administering device into the interior of the piston rod 5 and terminates in the front region of the piston rod 5. A second spring 14 is inserted within the recess 13 and is mounted via one end on the base of the recess 13 and via another end on a closing wall 15 of the drive sleeve 2. The inner part of the piston rod 5, surrounded by the second spring 14, protrudes as an extension 16 beyond the outer part of the piston rod 5 lying outside the second spring 14.

In an initial state, the extension 16 protrudes through an opening in the closing wall 15 of the drive sleeve and an opening in the wall 12 fixed to the casing, and is fixed by the trigger 8, wherein the first spring 11 and the second spring 14 are biased. One or more locking members or segments 17 are mounted between the sleeve part 2' and the sleeve part 2" of the drive sleeve 2. The locking segments 17 engage with a groove 18 arranged on the piston rod 5 in the circumferential direction and are held in this engagement by an inner wall of the casing. The locking segments 17, together with the groove 18, form a latching device which fixes the piston rod 5 with respect to the drive sleeve 2.

The locking segments 17 can be provided, for example, by a biased ring. In some preferred embodiments they are formed by a number of spheres or arc-shaped segments. In the case of spheres, this causes points to press between the piston rod 5 and the casing 1, and in the case of arc-shaped segments causes areas to press. Small skirts are provided on the sleeve parts 2' and 2", adjacent to the locking segment 17, which hold the locking segments in position.

Figure 2:
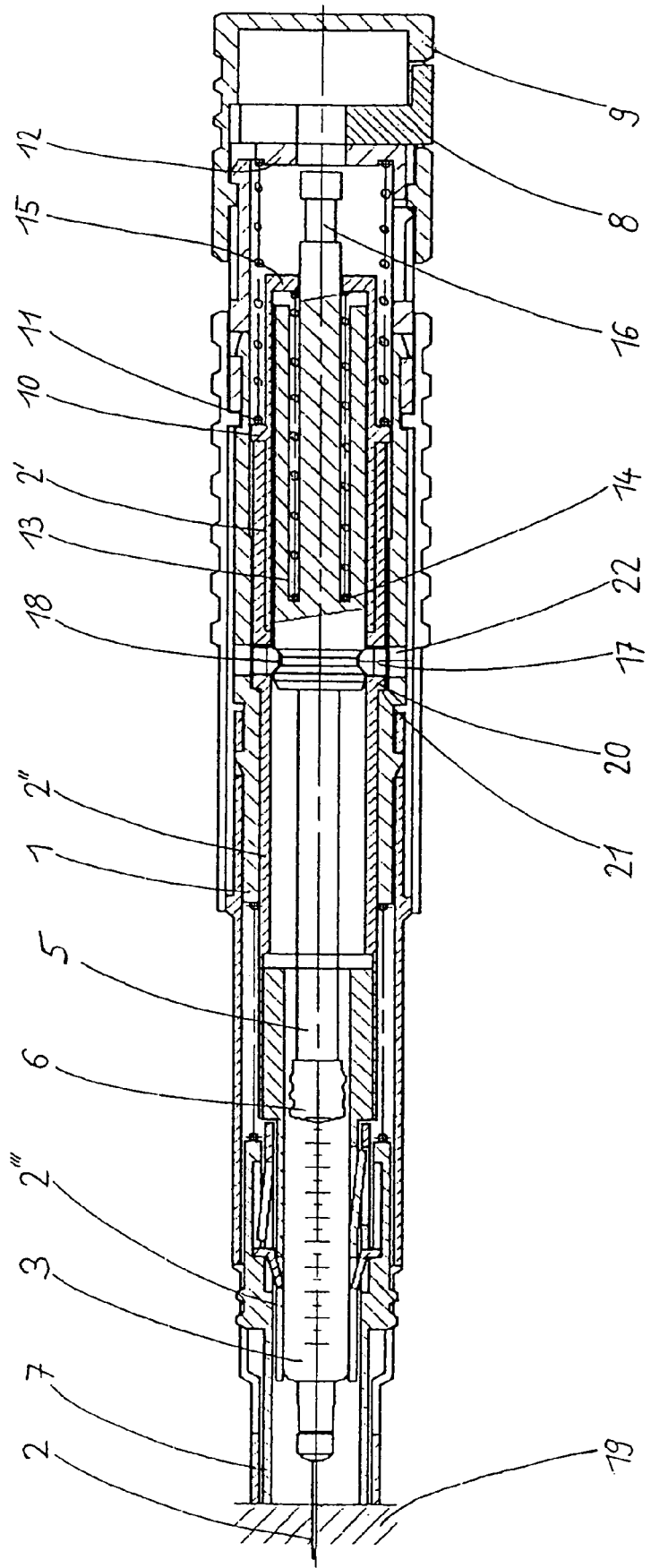
FIG. 2 is a longitudinal section through an administering device in accordance with the present invention in an insertion position.

FIG. 2 shows the administering device in an insertion position. The administering device has been placed on the tissue 19 and the needle protecting sleeve 7 retracted into the casing 1. The trigger 8 has been activated and the extension 16 of the piston rod 5 thereby released. The action of the force of the first spring 11 moves the drive sleeve 2 in the insertion direction relative to the casing 1 and inserts the injection needle 4 into the tissue 19. The drive sleeve 2 is shifted relative to the casing 1 until it abuts an insertion stopper 21 on the casing 1 via a heel 20. The heel 20 striking the insertion stopper 21 stops the insertion movement of the drive sleeve and the injection needle 4 is situated in an inserted state. In this insertion position, the locking segments 17 come to rest opposite a cavity 22, encircling in the circumferential direction, in an inner wall of the casing 1. The cavity 22 forms a releasing device for releasing the delivery means. The locking segments 17, such as for instance arc-shaped segments or spheres, drop into the cavity 22 and thereby release their engagement with the groove 18 of the piston rod 5. The piston rod 5 thus ceases to be fixed with respect to the drive sleeve 2 and the force of the second spring 14 drives the piston rod 5 in the insertion direction with respect to the drive sleeve 2. This shifts the piston 6 within the ampoule 3 and administers the product through an outlet in the ampoule and the injection needle.

Figure 3:
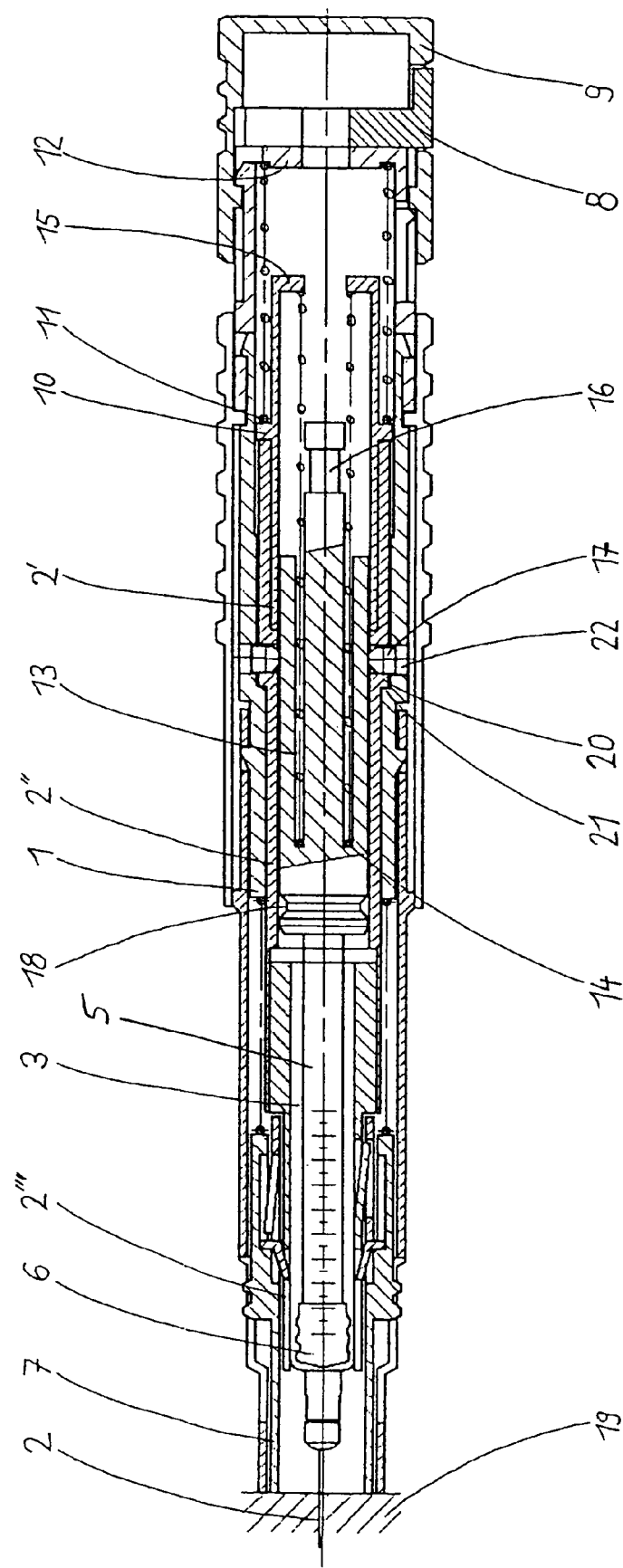
FIG. 3 is a longitudinal section through an administering device in accordance with the present invention in a delivery position.

FIG. 3 shows the administering device in a delivery position. The piston rod 5 is in an advanced position in which the piston 6 is in a front position in the ampoule 3. It is also conceivable to provide a dosing means within the administering device, which can set a stopper for the piston rod 5 in the longitudinal direction of the administering device in such a way that the distance which the piston rod 5 travels is limited in accordance with a desired product dosage.

The administering device is reusable. To this end, the drive sleeve 2 and the piston rod 5 can be returned to their rear position, wherein the first spring 11 and the second spring 14 are biased (or tensioned) and fixed or held in this initial position by the trigger 8. This step could, for example, be performed together with inserting a new ampoule into the administering device. The locking segments 17 and the skirts on the sleeve parts 2' and 2" are advantageously formed such that when the piston rod 5 is moved back, the locking segments 17 re-engage with the groove 18, such that the piston rod 5 is latched to the drive sleeve 5.

Other ways of embodying an administering device of the present invention are possible without deviating from the principles of the invention. For example, it is conceivable to fix the first and second spring at their points of application on the casing, the drive sleeve and the piston rod and to generate a bias on the springs by expanding the springs, for example by moving the casing with respect to the drive sleeve and the piston rod. Furthermore, in a variant of the drive sleeve and piston rod, a rod could be provided for driving the insertion means and a sleeve or cylinder provided as a drive member of the delivery means.

Embodiments of the present invention, including preferred embodiments, have been presented for the purpose of illustration and description. They are not intended to be exhaustive or to limit the invention to the precise forms and steps disclosed. Obvious modifications or variations are possible in light of the above teachings. The embodiments were chosen and described to provide the best illustration of the principles of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A device for administering an injectable product, comprising:
   an outer casing;
   a drive sleeve positioned within the outer casing and axially movable with respect to the outer casing;
   a first pressure element for driving the drive sleeve distally with respect to the outer casing;
   a piston drive member positioned within the drive sleeve and axially movable with respect to the drive sleeve;
   a second pressure element for driving the piston drive member distally within the drive sleeve;
   a piston for acting on the injectable product when acted upon by the piston drive member; and
   a trigger configured to establish a releasable engagement with the piston drive member in a proximal position prior to operation of the device, wherein activation of the trigger releases the engagement between piston drive member and the trigger, thereby triggering distal movement of the drive sleeve from an initial position to a needle insertion position by the first pressure element and triggering distal movement of the piston drive member by the second pressure element to drive the piston, wherein the piston drive member is at rest relative to the drive sleeve until the drive sleeve has reached the needle insertion position.

2. The administering device as set forth in claim 1, wherein the first and the second pressure elements are arranged along a longitudinal axis of the device.

3. The administering device as set forth in claim 2, wherein the first and the second pressure elements are springs.

4. The administering device as set forth in claim 1, further comprising a latch whereby the piston drive member can be fixed to the drive sleeve.

5. The administering device as set forth in claim 4, wherein said latch is on an insertion stopper which co-operates with a releasing device to release the piston drive member from the drive sleeve.

6. The device as set forth in claim 1, wherein the piston drive member is moved distally relative to the drive sleeve by said second pressure element when the needle insertion position has been reached.

7. The administering device as set forth in claim 1, wherein the second pressure element is at rest while the drive sleeve is driven.

8. The administering device as set forth in claim 1, wherein said trigger acts directly on the piston drive member.

9. The administering device as set forth in claim 1, wherein the drive sleeve comprises generally co-axially arranged sleeve parts.

10. An administering device comprising:
  a casing;
  a drive sleeve accommodated in the casing and comprising generally co-axially arranged sleeve parts comprising a first sleeve part which receives a product container and an injection needle in such a way that the injection needle is generally adjacent to a first end of the casing and extends out of said first sleeve part;
  a drive member arranged within second and third sleeve parts and operably coupled to a piston in the product container, said drive member comprising a rear portion defining a recess and an inner part extending as an extension beyond a portion of the drive member and the casing;
  a needle protecting sleeve moveably carried at the front end of the casing to cover and expose the injection needle;
  a trigger for triggering the drive sleeve and the drive member, the trigger adjacent to a second end of the casing, opposite to the front end of the casing, and extending laterally out of the casing, said trigger operably coupled to said extension;
  a first spring extending generally between a protrusion associated with the second sleeve part and the casing;
  a second spring in the recess and having a first end contacting said drive member and a second end operably contacting the drive sleeve; and
  a releasable latch comprising at least one locking member generally between the second and third sleeve parts for releasable engagement with at least one groove on the drive member, said at least one locking member held in the at least one groove by the casing, said latch releasably fixing the drive member and the drive sleeve;
  wherein the trigger engages said extension of the drive member in a proximal position prior to operation of the device, wherein activation of the trigger releases the drive member, thereby triggering distal movement of the drive sleeve from an initial position to a needle insertion position by the first spring and triggering distal movement of the drive member by the second spring to drive the piston, wherein the releasable latch holds the drive member at rest relative to the drive sleeve until the drive sleeve has reached the needle insertion position.

11. The device according to claim 10, wherein the at least one locking member comprises one of a number of spheres or a number of arc-shaped segments.

12. The device according to claim 11, wherein said second and third sleeve parts comprise skirts adjacent to the at least one locking segment to hold said spheres or segments.

* * * * *